US00PP27345P3

(12) United States Plant Patent
Wagner, Sr.

(10) Patent No.: US PP27,345 P3
(45) Date of Patent: Nov. 1, 2016

(54) ***ZOYSIA JAPONICA* L. PLANT NAMED 'SS-Z15'**

(50) Latin Name: ***Zoysia japonica* L.**
Varietal Denomination: SS-Z15

(71) Applicant: Sod Solutions, Inc., Mount Pleasant, SC (US)

(72) Inventor: Tobey Andrew Wagner, Sr., Mount Pleasant, SC (US)

(73) Assignee: Sod Solutions, Inc., Mount Pleasant, SC (US)

( * ) Notice: Subject to any disclaimer, the term of this patent is extended or adjusted under 35 U.S.C. 154(b) by 129 days.

(21) Appl. No.: 14/121,393

(22) Filed: Aug. 30, 2014

(65) Prior Publication Data

US 2015/0067937 P1 Mar. 5, 2015

Related U.S. Application Data

(60) Provisional application No. 61/959,719, filed on Aug. 30, 2013.

(51) Int. Cl.
*A01H 5/12* (2006.01)

(52) U.S. Cl.
USPC ..... Plt./390
CPC ..... *A01H 5/12* (2013.01)

(58) Field of Classification Search
USPC ..... Plt./390
See application file for complete search history.

*Primary Examiner* — Annette Para
(74) *Attorney, Agent, or Firm* — Myers Bigel & Sibley, P.A.

(57) ABSTRACT

A new and distinct cultivar of *Zoysia* grass named 'SS-Z15', is characterized by its wide leaf blade, long white inflorescences, slow lateral growth and good cold hardiness, compared to other *Zoysia* grass cultivars.

4 Drawing Sheets

Latin name of the genus and species: The Latin name of the genus and species of the novel cultivar disclosed herein is *Zoysia japonica* L. and therefore characterizes a new and distinct perennial cultivar of *Zoysia*.

Variety denomination: The inventive cultivar of *Zoysia japonica* L. disclosed herein has been given the variety denomination 'SS-Z15'.

BACKGROUND OF THE INVENTION

The present invention relates to a new and distinct perennial cultivar of *Zoysia japonica* L., hereinafter referred to by the cultivar name 'SS-Z15'.

'SS-Z15' is the selection of *Zoysia japonica* chosen at the Sod Solutions research center in 2008. The exact pedigree is unclear as the plant was selected in the proximity of two *Zoysia* grasses including the purple stemmed japonica 'Meyer' *Zoysia* and 'BK-9' *Zoysia*, which is *Z. japonica*×*Z. tenufolia*. 'SS-Z15' was selected due to a distinct green stem and relative short leaf blades that were light green color. 'SS-Z15' has been evaluated in Florida, Texas, North Carolina, Kentucky and Mississippi in test plot areas during 2009. The primary characteristics of the 'SS-Z15' are course texture, wide leaf blade, relative short blades compared to the width, long white inflorescence and a pale color seed head. 'SS-Z15' has demonstrated excellent fall color retention, good cold hardiness and green stolons. The rate of growth is good with average aggressiveness which is beneficial to a low maintenance grass. In field applications, 'SS-Z15' has faster runner growth rates than 'Meyer'. 'SS-Z15' is so identified in pictures and morphological and agronomic charts of this disclosure.

'SS-Z15' has been found to retain its distinctive characteristics through successive asexual propagations.

SUMMARY OF THE INVENTION

'SS-Z15' is a distinctive cultivar of *Zoysia japonica* L. having a light green color, relative course leaf texture, long white inflorescence, average lateral growth rates and good cold tolerance. 'SS-Z15' is propagated by sprigs, rhizomes, plantlets, and/or turf sod. 'SS-Z15' is estimated to be adapted for use in zones 7-11 of the Plant Heat Zone Map.

BRIEF DESCRIPTION OF THE FIGURES

This new *Zoysia* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Zoysia*.

DETAILED BOTANICAL DESCRIPTION

The following is a detailed description of the new *Zoysia* grass cultivar, based upon observations of the plant grown in field plots at a research area located near Starkville, Miss.

All colors cited herein refer to the Munsell Color Chart. 'SS-Z15' is an outstanding *Zoysia* grass cultivar with a unique light green color, green stems (7.5GY8/10) with no purple runners making it an attractive monolithic grass. 'SS-Z15' performs better in warmer climates and although it has good cold tolerance is best suited for Plant Heat Zones 7-11. 'SS-Z15' is a lower maintenance grass due to its reduced aggressiveness and its relative lower density than other *Zoysia japonica* varieties.

Color and Dimensions of Morphological Structures

'SS-Z15' has green leaves (7.5GY 6/6) and green stems (7.5GY 8/10) with light green internodes (stolons) (5GY/6/6). The flower of 'SS-Z15' is white (N 9.5/) and the seed head is pale yellow (5Y8/6).

Figure 1:
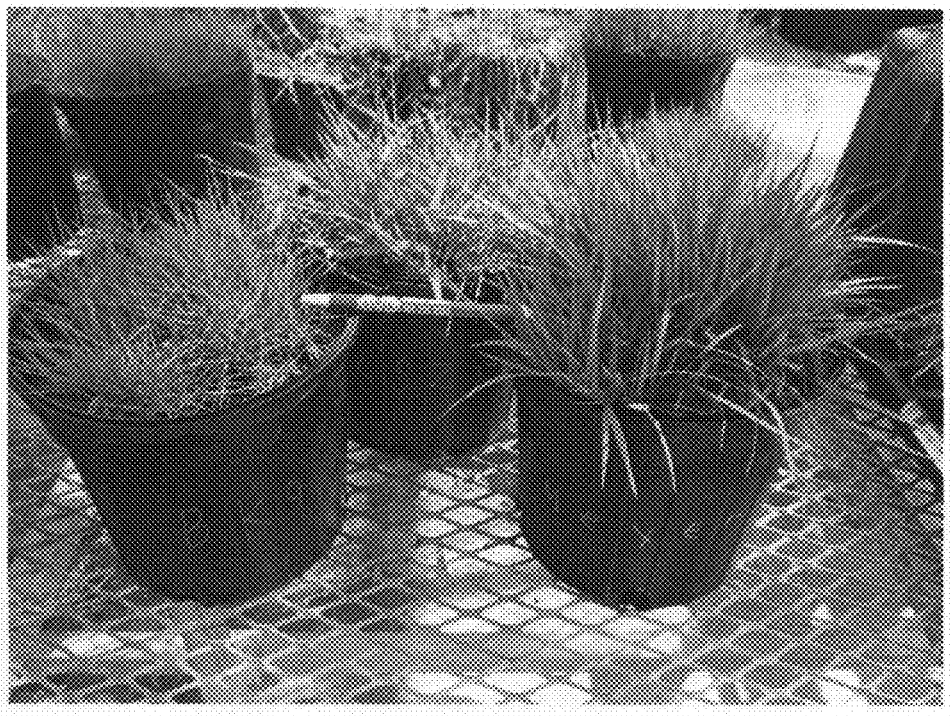
FIG. 1. shows 'SS-Z15' planted in pots at green-house in a research area; Starkville, Miss. 'SS-Z15' is shown in the middle, 'Meyer' *Zoysia* on the right and 'BK-9' on the left.
Figure 2:
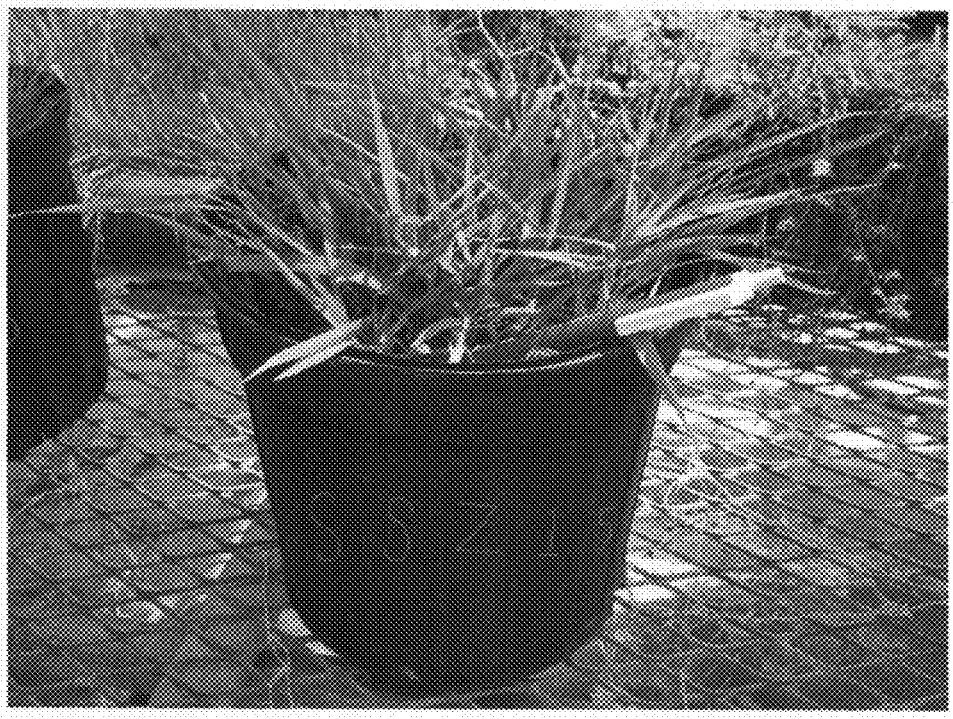
FIG. 2 shows 'SS-Z15' pot for evaluation inside a greenhouse near Starkville, Miss.

'SS-Z15' was compared to three other *Zoysia* grass cultivars in a study planted near Starkville, Miss. starting in August 2010. Each cultivar was planted in 1 gallon pots, using potting mix: Redi-earth Plug and Seedling Mix (Sungro Horticulture, Bellevue, Wash.) and were kept at a green-house to produce plant material for morphological evaluations. Plant material was collected using a random experimental design with 4 replications (pots). The greenhouse complex provided natural sunlight conditions. The pots were allowed to grow for four weeks, and then the plants were clipped once to encourage density and stolon development. The plants were allowed to grow un-mowed for another 4 weeks before measurement. The leaf blade measurements were conducted from Aug. 26, 2010 through Oct. 7, 2010. Seventy randomly selected leaf blades from each cultivar were measured for length and width. Width was measured at the widest point of the blade. The internode measurements were conducted from Nov. 1-12, 2010. All the stolons that grew off each pot were used to measure the internode diameter and internode length. The inflorescence measurements were conducted from Dec. 14, 2010 through Mar. 2, 2011. Twenty five seed-heads were randomly selected from each cultivar. Three florets were randomly selected from each head for measurement. FIG. 1 and FIG. 2 show the plants in greenhouse during evaluation.

The Analysis of Variance (ANOVA) indicated that cultivars differed significantly for most variables measured (Table 1).

TABLE 1

Analysis of Variance for comparison of 'SS-Z15'with other *Zoysia* grass cultivars conducted during the 2010 and 2011 growing seasons.

| | Mean Squares of the traits | | | | |
|---|---|---|---|---|---|
| Source | ID (mm) | IL (mm) | LL (mm) | LW (mm) | TIL (mm) |
| Cultivar | 12.1** | 1986.9* | 20231.6** | 1128.4** | 34684.1** |
| Error | 0.09 | 69.30 | 316.81 | 0.203 | 187.6 |
| CV | 17.18 | 34.60 | 23.99 | 12.63 | 14.61 |

| | Mean Squares of the traits | | | |
|---|---|---|---|---|
| Source | FRL (mm) | PL (mm) | NSI | SL (mm) |
| Cultivar | 2854.8** | 17989.1** | 2265.6** | 9.42* |
| Error | 12.28 | 161.8 | 21.15 | 0.06 |
| CV | 13.91 | 18.56 | 19.56 | 8.58 |

ID—Internode Diameter, IL—Internode Length, LL—Leaf Length (mm), LW—Leaf Width (mm), TIL—Total Inflorescence Length, FRL—Floral Region Length, PL—Peduncle Length, NSI—Number of Spikelets per Inflorescence, SL—Spikelet Length.
*Significant at 5% level
**Significant at 1% level The cultivars showed significant differences on many of the analyzed morphological characteristics (Table 1). Internode Diameter (ID), Internode Length (IL), Leaf Length (LL), Leaf Width (LW), Total Inflorescence Length (TIL), Floral Region Length (FRL), Peduncle Length (PL) and Number of Spikelets per Inflorescence (NSI) were significantly different at 1% level (Table 1). Spikelet Length (SL) was significantly at 5% level (Table 1). The evaluations were well conducted and produced reliable results as demonstrated by the low Coefficients of Variation (CV) (Table 1).

Figure 3:
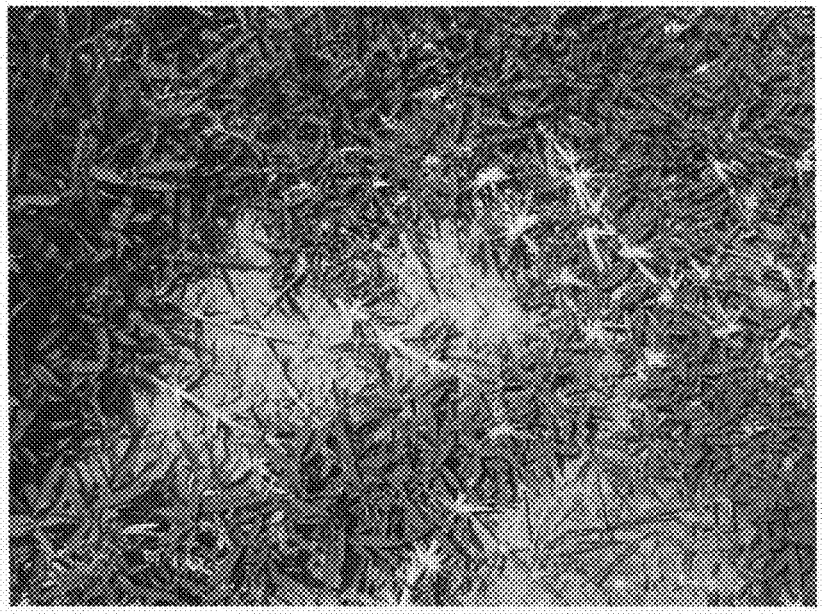
FIG. 3 shows the leaf detail of 'SS-Z15'.

'SS-Z15' has a larger internode diameter (2.20 mm) when compared to 'El Toro' and the other cultivars used as comparisons (Table 2). 'El Toro' is the cultivar that looks most similar to 'SS-Z15' with naked eye, in that both cultivars are considered to have 'coarse texture' (FIG. 3). 'SS-Z15' also has the widest leaf blade width (5.10 mm) among the tested cultivars (Table 2). 'El Toro' was the cultivar with the second widest leaf blade width (Table 2), but still significantly different from 'SS-Z15'. The leaf blade width difference between the two cultivars was 0.9 mm; which is greater than 0.2 mm, the least significant difference (LSD) at 5% level (Table 2).

TABLE 2

*Zoysia* cultivar comparisons with 'SS-Z15' conducted during 2010.

| | Internode | | Leaf Blade | |
|---|---|---|---|---|
| Cultivar | Diameter (mm) | Length (mm) | Width (mm) | Length (mm) |
| 'SS-Z15' | 2.2 | 25.8 | 5.1 | 83.4 |
| 'El Toro' | 2 | 30.2 | 4.2 | 80.1 |
| 'BK-9' | 1.4 | 23.3 | 2 | 48.8 |
| 'Meyer' | 1.6 | 18 | 3 | 84.4 |
| LSD(0.05) | 0.1 | 2.6 | 0.2 | 5.9 |

Figure 4:
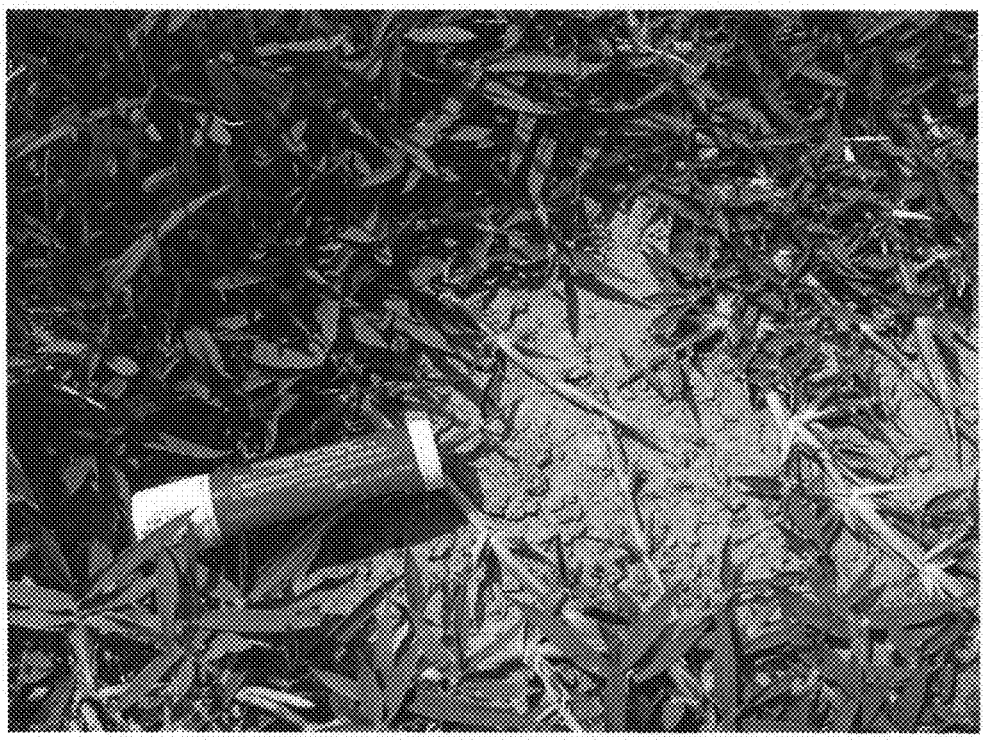
FIG. 4 shows the stolon/internode detail of 'SS-Z15'.

'SS-Z15' has a light green stolon similar to 'BK-9' and 'Meyer' (FIG. 4). Other distinctive characteristics of 'SS-Z15' are its large diameter and long internode. Table 2 shows 'El Toro' with the longest internode length (30.2 mm) and 'SS-Z15' with the second longest internode length (25.8 mm) among the tested cultivars. The difference between 'El Toro' and 'SS-Z15' (4.4 mm) was statistically different at the 1% level (Table 1). 'SS-Z15' also exhibits the largest internode diameter (2.2 mm), when compared to 'BK-9', 'El Toro' and 'Meyer' (Table 2). 'El Toro' exhibited the second largest internode diameter (2 mm), but still with a difference (0.2 mm) statistically different at the 5% level (Table 2).

Narrow and short leaf blades in combination with small internode diameter and short internode length (Table 2) provide 'SS-Z15' with a fine and dense aesthetic look. Normally, fine bladed *Zoysias* are spiked to the touch, making it unpleasant to step on or lay on top of. Despite having relative short blades length to width and short internodes, 'SS-Z15' is soft to the touch, providing a pleasant feeling when stepped on and touched.

Furthermore, short and narrow leaf blades (Table 2) enable 'SS-Z15' to produce less scalping when maintained with a rotary mower, when other so called 'fine bladed' *Zoysias* have to be maintained with reel mower to avoid scalping, due to longer and wider leaf blades.

Figure 5:
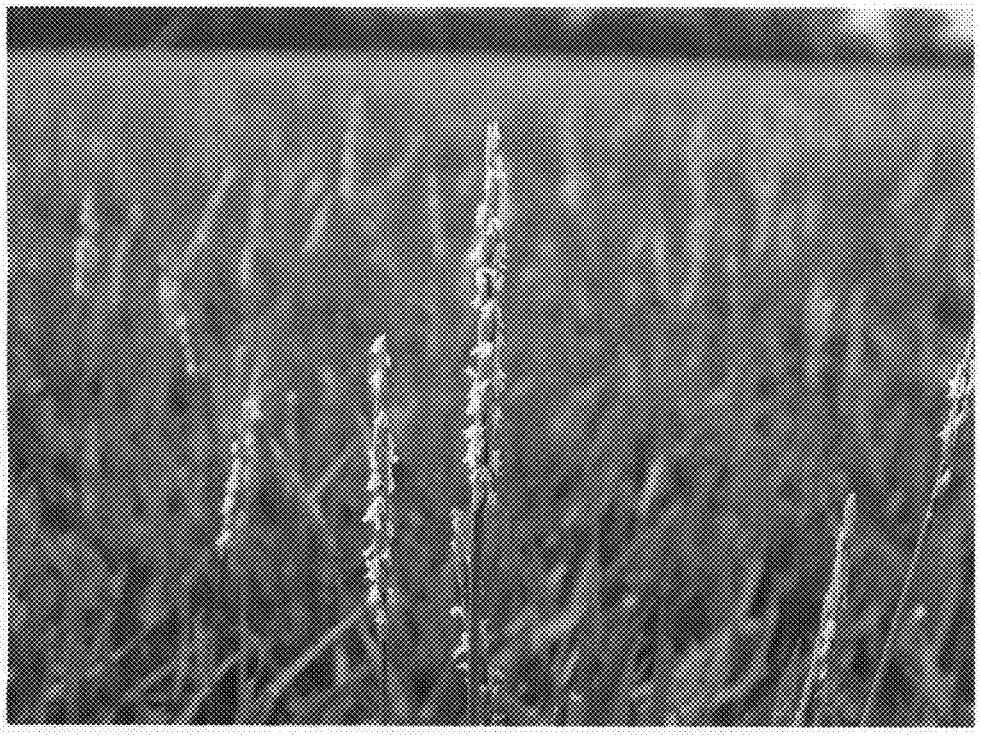
FIG. 5 shows the inflorescences of 'SS-Z15'.
Figure 7:
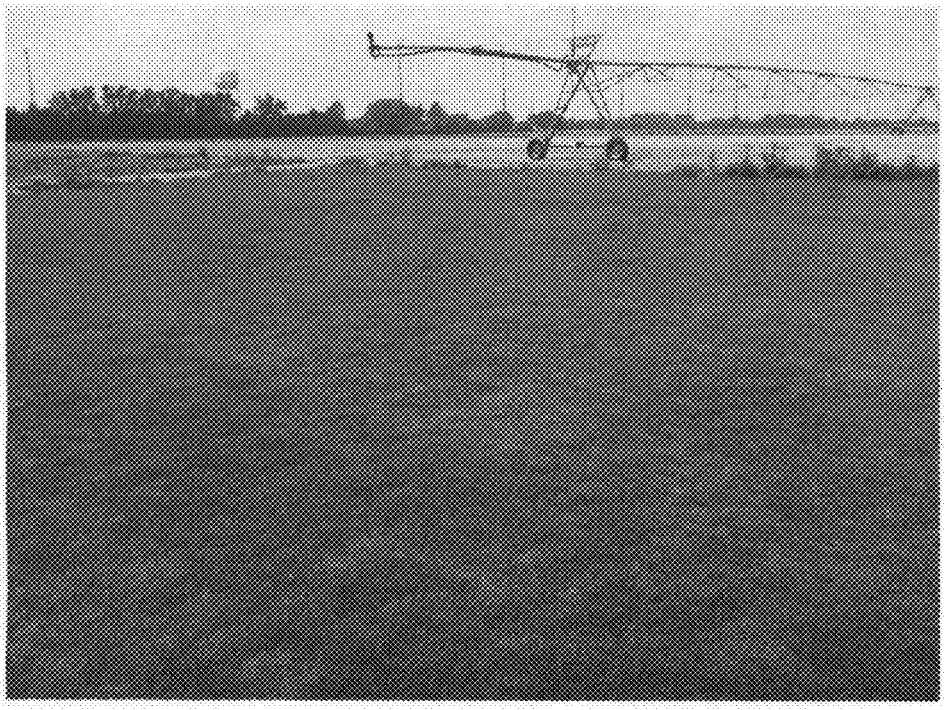
FIG. 7 shows 'SS-Z15' field showing overall green color.

'SS-Z15' has very large inflorescences, particularly long seed-heads (floral region) and peduncles (FIG. 5) compared to other *Zoysia* cultivars. The total inflorescence structure easily stands out in the plant canopy, making it difficult to be spotted and seeing by a person walking the field. The result is a more pleasant look of the grass field, with the predominant green color from the leaves and not the purple color from the floral structure (See, FIG. 7).

Figure 6:
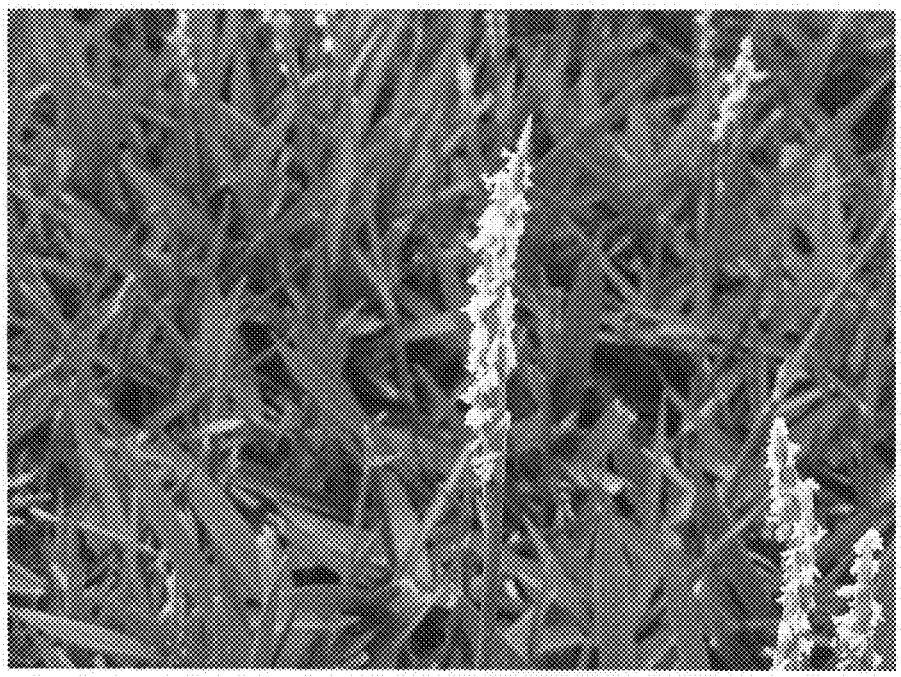
FIG. 6 shows flower structures of 'SS-Z15' blended in the canopy.

A more detailed examination of the inflorescence structures (See, FIG. 6), shows 'SS-Z15' has the longest floral region (36 mm) and peduncle (88.7 mm), compared to 'Meyer', 'El Toro' and 'BK-9' (Table 3). As a result, the total inflorescence length of 'SS-Z15' (124.7 mm) is the longest among all tested cultivars (Table 3). The cultivar with the second longest inflorescence structure is 'El Toro', with floral region length of 31.1 mm, peduncle length of 86.1 mm and total inflorescence of 117.3 mm (Table 3). Floral region length, peduncle length and total inflorescence length of 'SS-Z15' were statistically different than the respective floral structures of 'Meyer', 'El Toro' and 'SS-Z15' (Table 3). In addition of having the longest total inflorescence among the compared cultivars, 'SS-Z15' had the longest spikelet length (3.7 mm) compared to the other cultivars (Table 3). 'SS-Z15' spikelet length is statistically different from all other cultivars in that test (Table 3).

TABLE 3

*Zoysias* inflorescences compared to 'SS-Z15' conducted in 2010.

| Cultivar | Total inflorescence length [a] (mm) | Floral region length [b] (mm) | Peduncle length [c] (mm) | Number of spikelets per inflorescence [d] | Spikelet length [e] (mm) |
|---|---|---|---|---|---|
| 'SS-Z15' | 124.7 | 36.0 | 88.7 | 25.5 | 3.7 |
| 'El Toro' | 117.3 | 31.1 | 86.1 | 29.6 | 3.0 |
| 'Meyer' | 90.7 | 21.9 | 68.9 | 29.4 | 2.6 |
| 'BK-9' | 42.3 | 11.8 | 30.5 | 9.5 | 2.3 |
| LSD(0.05 ) | 7.7 | 2 | 7.1 | 2.6 | 0.1 |

[a] Total inflorescence length is the mean of 25 observations per cultivar including the floral region and peduncle.
[b] Floral region length is the mean of 25 observations per cultivar
[c] Peduncle length is the mean of 25 observations per cultivar measured from the base of the floral region to the first node.
[d] Number of spikelets per inflorescence is the mean of 25 observations per cultivar determined by count.
[e] Spikelet length is the mean of 3 observations per inflorescence and 75 per cultivar.

That which is claimed is:

1. A new and distinct cultivar of *Zoysia* grass named 'SS-Z15', as herein illustrated and described, characterized by its distinctive and unique combination of several characteristics such as: light green color, course texture, wide leaf blade with relative short blades, long white inflorescences, and green stolons.

* * * * *